United States Patent [19]

Osborne et al.

[11] Patent Number: 5,041,085
[45] Date of Patent: Aug. 20, 1991

[54] PERCUTANEOUS LOCKABLE SLEEVE CATHETER

[75] Inventors: Thomas A. Osborne, Bloomington; Fred T. Parker, Unionville, both of Ind.; John D. Roll, Rockford, Ill.

[73] Assignee: Cook Incorporated, Bloomington, Ind.

[21] Appl. No.: 485,269

[22] Filed: Feb. 26, 1990

[51] Int. Cl.⁵ ............................................ A61M 31/00
[52] U.S. Cl. ............................... 604/51; 604/95; 604/171; 604/178; 604/283
[58] Field of Search .................. 604/93, 95, 164, 165, 604/171, 174, 178, 280, 283, 905

[56] References Cited

U.S. PATENT DOCUMENTS

| | | | |
|---|---|---|---|
| 1,207,479 | 12/1916 | Bisgaard | 604/95 X |
| 3,119,392 | 1/1964 | Zeiss | 604/95 X |
| 3,394,954 | 7/1968 | Sarns | 604/905 X |
| 3,554,580 | 1/1971 | Goyke | 604/283 X |
| 3,924,633 | 12/1975 | Cook et al. | 128/349 R |
| 4,592,749 | 6/1986 | Ebling et al. | 604/283 |
| 4,740,195 | 4/1988 | Lanciano | 604/95 |
| 4,869,719 | 9/1989 | Hogan | 604/174 |
| 4,963,129 | 10/1990 | Rusch | 604/8 |
| 4,969,879 | 11/1990 | Lichte | 604/283 |

OTHER PUBLICATIONS

"Willis-Oglesby Percutaneous Gastrostomy Set", Cook Incorporated, Bloomington, Ind., 1984.
"Cook-Cope Type Loop Drainage Sets", Cook Incorporated, Bloomington, Ind., 1983.
Roll et al., "Simplification of the Cope Loop Catheter," Seminars in Interventional Radiology, vol. 4, No. 1, Mar. 1987, p. 46.

Primary Examiner—John D. Yasko
Assistant Examiner—Adam J. Cermak
Attorney, Agent, or Firm—Richard J. Godlewski

[57] ABSTRACT

A lockable sleeve drainage catheter is disclosed for percutaneous insertion into a patient and drainage of fluid therefrom. The drainage catheter includes a flexible distal end that is preformed for retaining the distal end of the catheter that is inserted in the patient. For insertion, the distal end is straightened with the use of a stiffening cannula that is inserted through the hollow passageway of the catheter. When the catheter is inserted in the patient, the stiffening cannula is removed, and a flexible tension member positioned within the passageway of the catheter is drawn to position the distal end in the desired retention configuration. A lockable sleeve positioned at the proximal end of the catheter draws the flexible tension member through the passageway of the elongated member tube to position the distal end in the retention configuration. The catheter also includes a locking collar at the proximal end of the elongated member tube having an annular recess formed therein. The distal end of the lockable sleeve includes an annular step for engaging the recess of the collar and locking the sleeve in a fixed position relative to the elongated member tube of the catheter. When fully extended and locked, the sleeve and elongated member form a fluid tight interconnection. A Luer lock connector is affixed to the proximal end of the sleeve for connection to a drainage collection system.

21 Claims, 3 Drawing Sheets

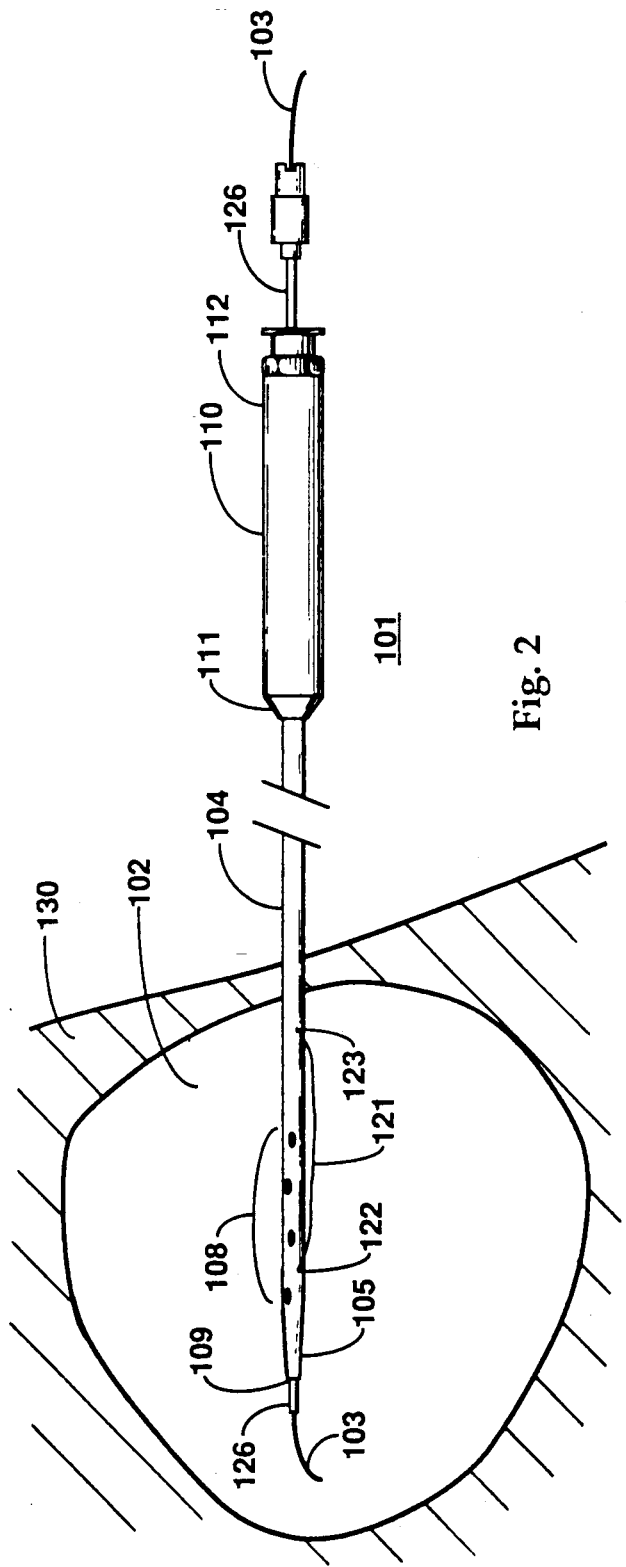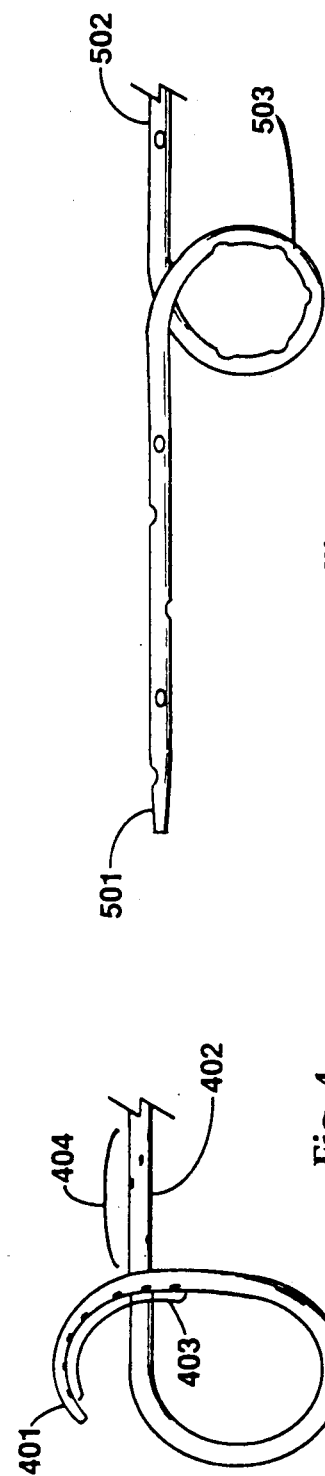
Fig. 2
Fig. 4
Fig. 5

PERCUTANEOUS LOCKABLE SLEEVE CATHETER

TECHNICAL FIELD

This invention relates to catheters and particularly to a catheter having a lockable sleeve for drawing the distal end into a predetermined configuration.

BACKGROUND OF THE INVENTION

Suprapubic catheterization of the bladder is used to drain the bladder after surgery or when the genitourinary system is plugged by an obstruction. Other percutaneously inserted catheters are also used to drain the kidney or biliary system as well as to drain abscesses, other sites of fluid collection and other viscera. Still other percutaneously inserted catheters are gastrostomy feeding tubes.

These catheters are introduced into the patient by means of a large hypodermic needle or trocar which typically pierces the abdominal wall. A wire guide is inserted through the needle, which is then removed. The catheter tube with a stiffening cannula positioned therein is then passed over the wire guide into the cavity. The cannula and wire guide are withdrawn, leaving the catheter in the desired cavity. With respect to the bladder, the advantage of this technique is that irrigation and infection of the urinary tract is minimized. However, one problem with these catheters is that the catheter can be easily pulled out by movement of the body or by the emptying of, for example, the bladder. Another problem is that side ports at the distal end of the catheter may be inadvertently drawn into the abdominal cavity creating potential for severe infections.

Various catheters have been developed with so-called pigtail loops at their distal ends which both ensures drainage of the cavity and prevents accidental removal therefrom. The pigtail loop is tightened by pulling on the proximal end of a flexible tension member which extends through the catheter. The proximal end of this tension member is held in place by any one of a number of retention means. In U.S. Pat. No. 1,207,479 to Bisgaard, the proximal end of the tension member is held in place by axially placing a hollow cap into or over the proximal end of the catheter tube, thus trapping the flexible tension member of which the protruding end may then be cut.

In other catheter developed by one of the present inventors and described in U.S. Pat. No. 3,924,677, the flexible tension member is trapped between two or more hollow tubes, one of which is slidably inserted axially into the other. A short length of the flexible member is generally left hanging from the catheter tube so that if the tension member becomes loose, it may be retightened.

In a second generation of this flexible member catheter, an external sleeve is slid over the flexible member protruding from the side of the catheter tube of which the flexible member is then wound around and tied about the sleeve.

Although well suited for its intended purpose, the physician is required to grasp and pull on the flexible tension member and to either secure or tie it about the proximal end of the catheter. Such a flexible tension member left exposed at the proximal end allows the patient to untie the member. As a result, the assistance of hospital personnel is required to retie the member. Furthermore, when the flexible tension member is inadvertently released, the retaining loop at the distal end is released with the possibility of the catheter being withdrawn from the patient.

SUMMARY OF THE INVENTION

The foregoing problems are solved and a technical advance is achieved in an illustrative lockable sleeve medical device such as a drainage catheter for insertion into a cavity or passageway of a patient. The lockable sleeve at the proximal end of the catheter draws the distal end of the catheter into a predetermined configuration, such as a pigtail loop, for retaining the catheter in the cavity or passageway of the patient. The catheter comprises a flexible elongated member, such as a flexible polymer material tube, having distal and proximal ends with a hollow passageway therebetween. Positioned about the distal end of the elongated member tube is a plurality of drainage ports for fluid to enter and drain through the tube. Also positioned about the distal end are first and second draw ports for positioning a flexible tension member therethrough, which is drawn to position the distal end of the tube into the predetermined configuration after the distal end of the tube is inserted into the cavity or passageway of the patient. When so positioned, the configured distal end prevents retraction of the catheter from the patient.

The improvement over the prior art comprises a lockable sleeve having a hollow passageway therein for receiving the proximal end of the elongated member. The flexible tension member is attached to the proximal end of the sleeve through the passageway of both the sleeve and elongated member to draw the distal end of the elongated member into the predetermined configuration. The sleeve also includes a projection positioned about the distal end thereof and extending into its passageway for engaging a recess in the proximal end of the elongated member. The flexible tension member is drawn by pulling the lockable sleeve longitudinally with respect to the proximal end of the elongated member. When the sleeve is fully extended to the proximal end of the elongated member, the projection in the sleeve engages the recess at the proximal end of the elongated member to fixedly position and lock the position of the sleeve relative to the elongated member. As a result, the distal end of the elongated member is drawn into the predetermined configuration, which prevents retraction of the catheter from the patient. Advantageously, the distal end of the elongated. member is drawn into the pigtail configuration without the physician having to cut or tie the free end of the flexible tension member. Whereas with the present invention, the distal end of the elongated member is drawn into the desired configuration with the simple motion of the physician pulling longitudinally on the sleeve with respect to the elongated member.

To minimize, if not eliminate, the drainage of fluid between the distal end of the sleeve and the proximal end of the elongated member, a further improvement includes a collar having the recess formed therein and positioned about the proximal end of the elongated member. The recess comprises a groove or annular channel extending circumferentially in the outer surface of the collar.

To further secure and minimize fluid drainage from around the proximal end of the elongated member and the distal end of the sleeve, the sleeve projection comprises an annular ridge that extends into the sleeve passageway at the distal end thereof and is sized to fit tightly in the annular channel of the collar. Alternatively, the projection comprises an annular step at the distal end of the sleeve that is also sized to snap fit into the annular channel of the collar. Furthermore, the dimension of the opening through the annular step is less than the maximum outside surface dimension of the annular channel to provide an extremely tight and leak resistant fit. This further enhances the ability of the catheter to minimize fluid drainage at the joined interconnection of the sleeve and elongated member.

A connector is suitably attached about the proximal end of the sleeve for connection to a fluid collection system. In addition, the flexible tension member is attached to the proximal end of the sleeve and extends through at least one of the draw ports at the distal end of the elongated member to draw the distal end of the elongated member into the predetermined configuration. A plurality of side ports at the distal end of the elongated member allow entry of the fluid into the tube and drainage through the passageway to the collection system.

BRIEF DESCRIPTION OF THE DRAWING

FIG. 2 depicts a partially-sectioned view of the catheter of FIG. 1 inserted in the bladder of a patient;

FIG. 4 depicts an alternative embodiment of the distal end of the catheter for use in the biliary system of a patient; and FIG. 5 depicts a second alternative embodiment of the distal end of the catheter for use as a gastrostomy feeding tube.

DETAILED DESCRIPTION

Figure 1:
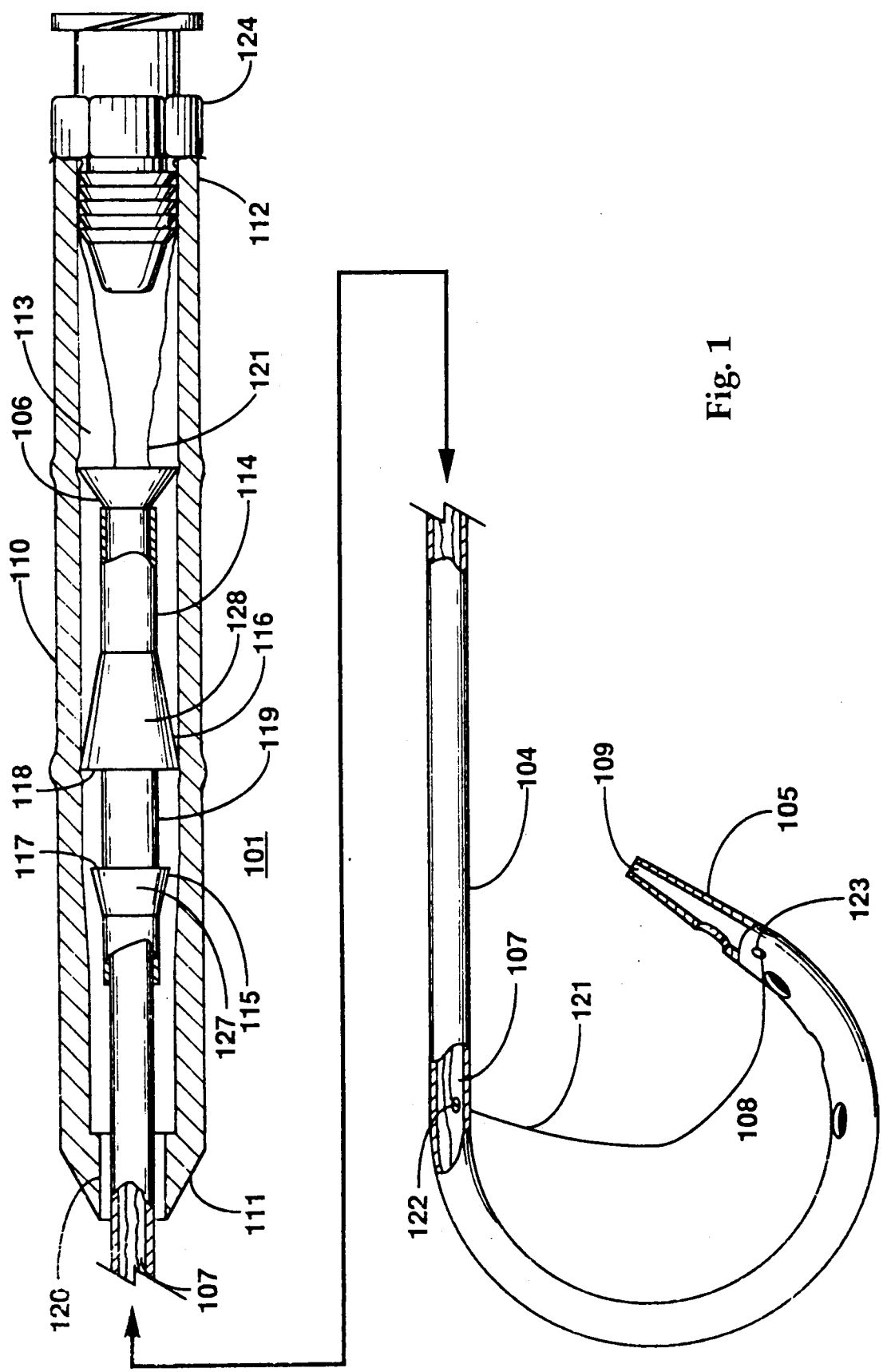
FIG. 1 depicts a lockable sleeve drainage catheter of the present invention.

Depicted in FIG. 1 is a partially-sectioned view of an illustrative lockable sleeve drainage catheter 101 in a relaxed and unlocked position prior to percutaneous insertion into a bladder.

Depicted in FIG. 2 is catheter 101 with stiffening cannula 126 inserted into bladder 102 over wire guide 103. Before insertion of catheter 101, a thinwall needle with a stylet inserted therein (not shown) is percutaneously inserted through abdominal wall 130 into the bladder using a well-known technique. The stylet is removed, and the wire guide is inserted through the needle into the bladder. The needle is then removed with the wire guide left in place. A dilator is commonly used over the wire guide to increase the size of the puncture site. Drainage catheter 101 with a stiffening cannula inserted therein is then inserted over the wire guide into bladder 102 as shown.

As shown in FIGS. 1 and 2, catheter 101 includes an elongated member 104 and a lockable sleeve 110, formed from flexible plastic material tubes having different diameters. Flexible member 104 has a tapered distal end 105, a flared proximal end 106, and a hollow longitudinal passageway 107 therebetween. Distal end 105 is preformed into a predetermined configuration such as a well-known pigtail. A plurality of side ports 108 are formed through the wall of the elongated member about the distal end thereof for fluid such as urine to enter and drain through passageway 107. Passageway 107 also forms an opening 109 at the very distal end of the elongated member. Opening 109 permits the insertion of the catheter into a patient over the wire guide and also allows further drainage of fluid into passageway 107. However, a stiffening cannula is normally inserted through passageway 107 of the catheter to straighten the preformed distal end for percutaneous insertion over the wire guide into the bladder. When the catheter has been inserted in the bladder, the stiffening cannula and wire guide are then removed from passageway 107.

Similarly, lockable sleeve 110 has a tapered distal end 111, a proximal end 112, and a hollow longitudinal passageway 113 therebetween. As previously indicated, both the elongated member and the lockable sleeve are formed from flexible plastic material tubes. By way of example, elongated member 104 is a 10.2 French polyurethane material tube approximately 32 cm in length, whereas lockable sleeve 110 is a 20 French polyurethane material tube approximately 6.5 cm in length. As shown, flared proximal end 106 of the elongated member tube and locking collar 114 affixed thereabout are positioned within sleeve passageway 113 and are longitudinally moveable therein.

The generally cylindrically-shaped locking collar includes two truncated cones 127 and 128 with beveled surfaces 115 and 116 facing the opposite ends of the collar. Base surfaces 117 and 118 of respective cones 127 and 128 and the outside surface 119 of the collar therebetween form an annular recess, such as a groove or channel, in the collar. Lockable sleeve 110 is longitudinally moveable over locking collar 114.

Distal end 111 of the lockable sleeve includes a projection 120, such as an annular ridge or step, which extends into passageway 113 to engage the annular recess of locking collar 114. As shown, annular step 120 at the tapered distal end 111 of the sleeve is sized to snap fit into the annular recess of collar 114 when the distal end of the sleeve is longitudinally moved over beveled surface 115. As a result, annular step 120 snaps into the annular recess of the collar. The minimum dimension or diameter of passageway 113 through annular step 120 is less than the maximum dimension or diameter of outside surface 119 of the collar in the annular recess. The two dimensions are sized to form a tight fit between the annular step and recess when interconnected, which prevents the passage of fluid through the interconnection. Beveled surface 116 of the collar and flared distal end 106 of the tube further prevent the passage of fluid through the interconnection.

The drainage catheter further includes flexible tension member 121 that passes through passageways 107 and 113 of elongated member tube 104 and lockable sleeve 110, respectively. Draw ports 122 and 123 are formed through the wall of the elongated member tube near drain ports 108. The flexible tension member passes from within passageway 107 through draw port 122 to the exterior of the elongated member and back into interior passageway 107 through draw port 123. The flexible tension member forms a loop through the draw ports, which is drawable to position the distal end of the elongated member tube into the desired pigtail configuration. The ends of the flexible tension member are secured to proximal end 112 of the lockable sleeve between the wall of the sleeve and the outside barbed surface of a well-known Luer lock connector 124. The flexible tension member, such as commercially available 4-0 Tevdek suture, is further secured between the two surfaces using, for example, Locktite 401 sealing compound.

When distal end 105 of elongated member tube 104 is fully extended for insertion into the bladder, lockable sleeve 110 is in a fully forward and unlocked position with the flared proximal end 106 of the tube positioned next to connector 124. Commonly, the Luer lock connector is formed with a taper at the distal end thereof. As a result, the flared proximal end 106 receives the tapered end of the Luer lock connector. The flared end fits against the wall of the sleeve to prevent the passage of fluid and flexible tension member therebetween.

Figure 3:
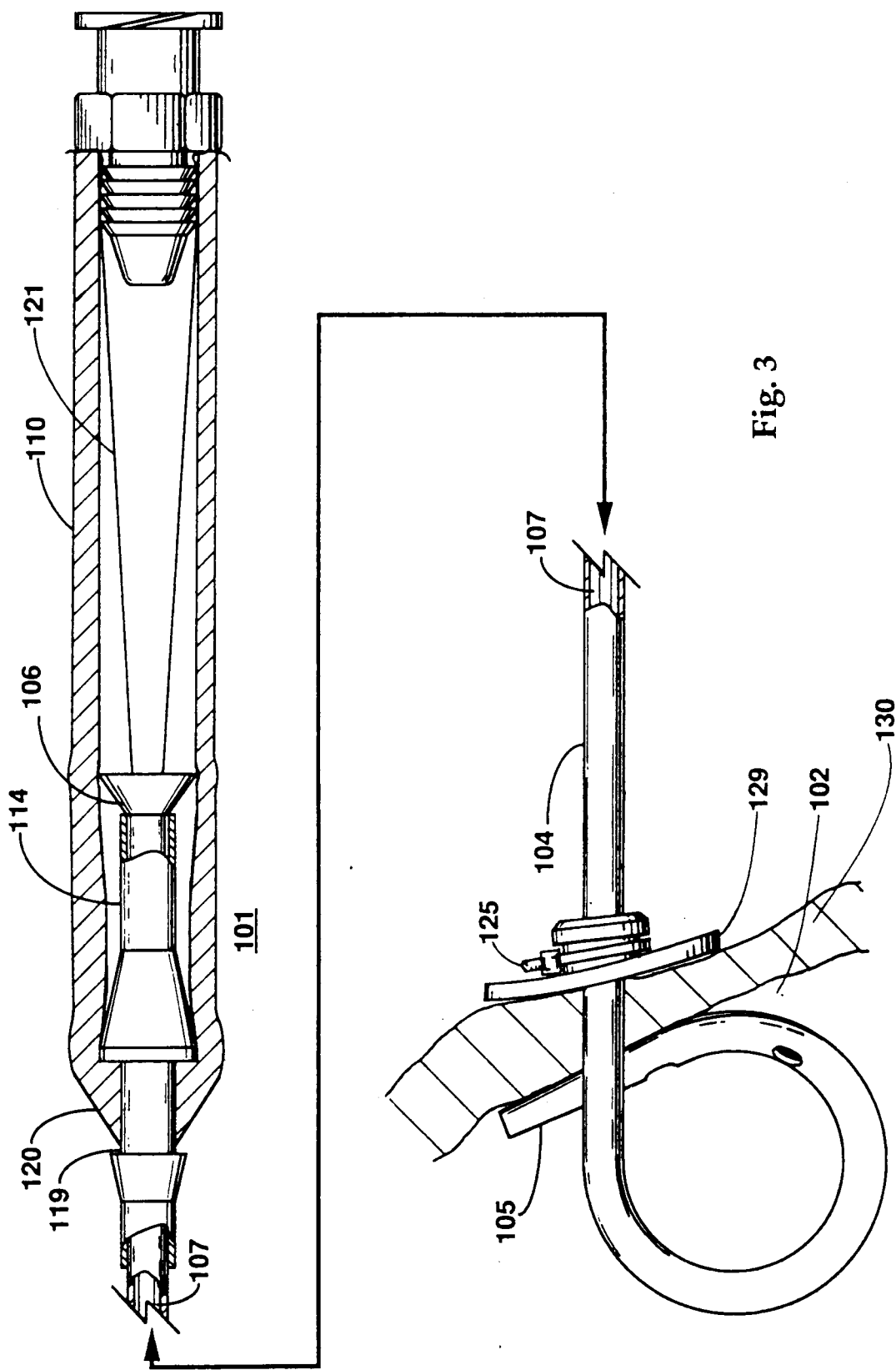
FIG. 3 depicts a partially-sectioned view of the catheter of FIG. 2 in a locked position.

Depicted in FIG. 3 is a partially-sectioned view of drainage catheter 101 with sleeve 110 in a fully drawn and locked position and distal end 105 positioned in the pigtail configuration. The pigtail configuration at the distal end of elongated member tube 104 acts as a retention device to prevent the catheter from being removed from the bladder. In the locked position, the sleeve has been longitudinally moved along the proximal end of the elongated member tube to engage annular step 120 with outside surface 119 in annular recess of collar 114. When the sleeve is pulled, the flexible tension member 121 is drawn through and out of elongated member passageway 107 to close the loop between draw ports 122 and 123, thereby positioning the distal end of the elongated member tube into the pigtail configuration. Retention disk 129 is applied to the outside surface of abdominal wall 130 around the elongated member with tie 125 to more securely position the drainage catheter in the patient. Retention disk 129 is commercially available from a number of sources such as Cook Incorporated, Bloomington, Ind. Flexible elongated member tube 104 may also be bent to run alongside the patient's body using a 90° retention disk also available from Cook Incorporated.

Depicted in FIG. 4 is an alternative embodiment of the distal end of the drainage catheter. In this particular embodiment, distal end 401 of elongated member 402 of the catheter has been preformed into a well-known configuration for retaining the distal end in the biliary system of a patient. A plurality of drainage ports 403 and 404 have been formed about the distal end and the main body of elongated member 402, respectively.

Depicted in FIG. 5 is a second alternative embodiment of the distal end of the elongated member portion of the drainage catheter. In particular, distal end 501 of elongated member tube 502 has been formed into a pigtail configuration with the distal end extending from pigtail curl 503. Such a configuration is suitable for use as a percutaneous inserted gastrostomy feeding tube.

It is to be understood that the above-described drainage catheter is merely an illustrative embodiment of the principles of this invention and that other apparatus and catheters may be devised by those skilled in the art without departing from the spirit and scope of this invention. In particular, the distal end of the catheter may be preformed into any desired configuration for positioning and retaining the distal end of the catheter in any part of a patient's body. Furthermore, the lockable sleeve of the drainage catheter may be designed with an 0-ring seal and the like for preventing fluid from passing through the joined interconnection of the sleeve and elongated member. Similarly, a single finger-like projection may extend into a recess formed in the proximal end of the elongated member tube. However, the illustrative embodiment illustrates a drainage catheter which is easily manipulated by the physician without having to tie the flexible tension member. Once in the locked position, the catheter maintains a closed system for which fluid may be drained from the patient. Furthermore, one end of the flexible tension member may be attached in any one of a number of well-known ways to the distal end of the elongated member and drawable through one or more draw ports for positioning the distal end and in the desired position.

What is claimed is:

1. A medical device comprising:
    an elongated member for insertion into a body and having a distal end, a proximal end, and a passageway extending longitudinally therebetween, said proximal end having a recess therein, said distal end being formed to be positioned into a predetermined configuration;
    an elongated sleeve having a distal end, a proximal end, and a passageway extending therebetween, said proximal end of said elongated member being positioned and longitudinally moveable within said sleeve passageway, said sleeve having a projection extending into said sleeve passageway about said distal end thereof and engageable with said recess to position longitudinally said sleeve relative to said elongated member; and
    a flexible tension member extending along said elongated member and said sleeve, fixedly positioned about said proximal end of said sleeve, and positioned and drawable about said distal end of said elongated member to position said distal end of said elongated member into said predetermined configuration.

2. The medical device of claim 1 further comprising a collar including said recess and positioned about said proximal end of said elongated member.

3. The medical device of claim 2 wherein said recess in said collar comprises an annular channel extending circumferentially in an outer surface of said collar.

4. The medical device of claim 3 wherein said projection comprises an annular ridge extending into said sleeve passageway about said distal end thereof and sized to fit tightly in said annular channel.

5. The medical device of claim 3 wherein said projection comprises an annular step at said distal end of said sleeve sized to snap fit into said annular channel and having an opening therein having a dimension less than a maximum outside dimension of said collar in said annular channel.

6. The medical device of claim 1 further comprising a connector positioned about said proximal end of said sleeve.

7. The medical device of claim 1 wherein said elongated member includes a plurality of ports about said distal end thereof, said flexible member extending in said passageway of said elongated member and external thereto between first and second of said ports and drawable with said sleeve to position said distal end of said elongated member into said predetermined configuration.

8. In a catheter including a flexible elongated member having a distal end, a proximal end, a passageway extending longitudinally between said ends, and first and second draw ports positioned about said distal end and also including a flexible tension member passing through at least one of said draw ports or, alternatively, attached about said distal end and drawable to position said distal end of said elongated member into a predetermined configuration;
    the improvement comprising:

a lockable sleeve having a distal end, a proximal end, and a passageway therebetween, said proximal end of said elongated member being movable within said passageway of said sleeve, said flexible tension member extending through said passageway of said elongated member and said sleeve and being attached to said sleeve;

a recess positioned about a proximal end of said elongated member and engageable with a projection received therein to longitudinally position said elongated member relative to said sleeve; and said sleeve also including said projection positioned about said distal end and extending radially in said passageway thereof.

9. The catheter of claim 8 wherein said improvement further comprises a collar positioned about said proximal end of said elongated member and including said recess therein.

10. The catheter of claim 8 wherein said recess comprises a groove positioned circumferentially around said collar.

11. The catheter of claim 10 wherein said projection comprises an annular ridge sized to tightly fit within said groove.

12. A drainage catheter comprising:

a flexible elongated member for insertion into a body of a patient and having a distal end, a proximal end, and a hollow passageway extending longitudinally therebetween, said distal end being formed to be positioned into a predetermined configuration and having a plurality of side ports including first and second draw ports;

a collar positioned about said proximal end of said elongated member and having an annular recess extending circumferentially in an outer surface thereof;

a lockable sleeve having a distal end, a proximal end, and a passageway extending therebetween, said proximal end forming an annular step extending into said sleeve passageway and engageable with said annular recess to position longitudinally said sleeve relative to said elongated member, said annular step being sized to fit tightly in said annular recess; and a flexible tension member extending through said passageway of said elongated member and said sleeve and said first and second draw ports and also exterior to elongated member between said first and second draw ports, fixedly positioned about said proximal end of said sleeve and drawable through said first and second draw ports to position said distal end of said elongated member in said predetermined configuration.

13. The method of percutaneously draining fluid from a cavity of a patient with a medical device comprising an elongated member having a distal end, a proximal end, and a passageway extending longitudinally therebetween, at least the distal end being for insertion, into the cavity of the patient; and means extending between the distal and proximal ends and drawable to reconfigure the distal end into a desired configuration; the device further comprising an elongated sleeve having distal and proximal ends with a passageway therebetween, the sleeve being positioned about and longitudinally moveable with respect to and adjacent to the proximal end of the elongated member; the drawable means being attached to the sleeve; and the elongated member within the sleeve and the interior of the sleeve having cooperating parts associated therewith for engaging the sleeve and the elongated member together when moved relative to one another to an engaging or interlocking position, comprising the steps of:

percutaneously inserting the distal end of the elongated member into the cavity of the patient;

moving the sleeve relative to the elongated member to the engaging or interlocking position; and connecting the sleeve to a fluid collection system.

14. The method of claim 13 further comprising the step of reconfiguring the distal end of the elongated member to the desired configuration.

15. The method of claim 14 wherein the step of reconfiguring includes drawing the drawable means in cooperation with moving the sleeve relative to the elongated member.

16. The method of claim 15 further comprising the step of engaging the cooperating parts of the sleeve and the elongated member to the engaging or interlocking position.

17. The method of claim 16 further comprising the step of forming a fluid-tight seal between the sleeve and the elongated member when the cooperating parts of the sleeve and the elongated member are in the engaging or interlocking position.

18. A medical device comprising an elongated member having a distal end, a proximal end, and a passageway extending longitudinally therebetween, at least the distal end being for insertion into a patient; and means extending between the distal and proximal ends and positioned and drawable to reconfigure the distal end into a desired configuration; characterized in that the device further comprises an elongated sleeve having distal and proximal ends with a passageway therebetween, the sleeve being positioned about and longitudinally moveable with respect to and adjacent to the proximal end of the elongated member; in that the drawable means is attached to the sleeve; and in that the elongated member within the sleeve and the interior of the sleeve have cooperating parts associated therewith for engaging the sleeve and the elongated member together when moved relative to one another to an engaging or interlocking position.

19. A device according to claim 18, characterized in that means are provided for clamping the drawable member relative to the proximal end of the sleeve; and in that the relative movement of the distal end of the sleeve towards the proximal end of the elongated member causes the drawable means to reconfigure the distal end of the elongated member into the desired configuration.

20. A device according to claim 18, characterized in that the cooperating parts comprise an annular ridge on the interior surface of the sleeve, and a cooperating recess associated with the exterior surface of the longitudinal member, the relative movement required to bring the ridge and the recess into cooperative engagement serving to provide the required movement of the drawable means.

21. A method of locating part of a medical device in a patient, said method comprising the steps of inserting at least the distal end of an elongated member in a cavity of the patient, and applying tension to a drawable member extending along the elongated member in order to reconfigure the distal end into a desired configuration thereby locking the distal end within the cavity, characterized in that the proximal end of the drawable member is attached to a sleeve longitudinally slidably positioned about the proximal end of the elongated member, and in that the tension is applied by moving the sleeve relative to the elongated member to a position in which the sleeve and elongated member engage or interlock.

* * * * *